US005763226A

United States Patent [19]
Wong et al.

[11] Patent Number: 5,763,226
[45] Date of Patent: Jun. 9, 1998

[54] *BACILLUS CEREUS* ENTEROTOXIN AND METHOD OF USE

[75] Inventors: Amy C. Lee Wong; Douglas J. Beecher, both of Madison, Wis.

[73] Assignee: Wisconsin Alumni Research Foundation, Madison, Wis.

[21] Appl. No.: 390,492

[22] Filed: Feb. 17, 1995

[51] Int. Cl.$^6$ .............................. A61K 39/07; C12P 21/00
[52] U.S. Cl. .................. 435/71.3; 435/71.1; 435/834; 424/234.1; 424/236.1; 424/246.1
[58] Field of Search ................................ 435/71.1, 71.3, 435/834; 424/234.1, 236.1, 246.1

[56] References Cited

U.S. PATENT DOCUMENTS 5,168,063  12/1992  Doyle et al.

OTHER PUBLICATIONS

Beecher, D.J. and Macmillan, J.D., (1990) A Novel Bicomponent Hemolysin from *Bacillus cereus*, Infection and Immunity, 58, pp. 2220–2227.

Beecher, D.J. and Macmillan, J.D., (1991) Characterization of the Components of Hemolysin BL from *Bacillus cereus*, Infection and Immunity, 59, pp. 1778–1784.

Beecher, D.J. and Lee Wong, A.C., (1994) Improved Purification and Characterization of Hemolysin BL, a Hemolytic Dermonecrotic Vascular Permeability Factor from *Bacillus cereus*, Infection and Immunity, 62, pp. 980–986.

Bitsaev, A.R. and Ezepchuk, Y.V., (1987) The Molecular Nature of the Pathogenic Effect Induced By *B. Cereus*, Mol. Genet. Mikrobiol. Virusol., 7, pp. 25–31.

Blum, H., Beier, H. and Gross, H.J., (1987) Improved silver staining of plant proteins, RNA and DNA in polyacrylamide gels, Electrophoresis, 8, pp. 93–99.

Carlson, C.R., Caugant, D.A. and Kolsto, A.-B., (1994) Genotypic Diversity among *Bacillus cereus* and *Bacillus thuringiensis* Strains, Applied and Environmental Microbiology, 60, pp. 1719–1725.

Christiansson, A., (1993) Enterotoxin production in milk by *Bacillus cereus*: a comparison of methods for toxin detection, Neth. Milk Dairy J., 47, pp. 79–87.

Fazekas, D.S G. and Scheidegger, D., (1980) Production of Monoclonal Antibodies: Strategy and Tactics, Journal of Immunological Methods, 35, pp. 1–21.

Gilmore, M.S., Cruz-Rodz, A.L., Leimeister-Wachter, M., Kreft, J. and Goebel, W., (1989) A *Bacillus cereus* Cytolytic Determinant, Cereolysin AB, Which Comprises the Phospholipase C and Sphingomyelinase Genes: Nucleotide Sequence and Genetic Linkage, Journal of Bacteriology, 171, pp. 744–753.

Glatz, B.A., Spira, W.M. and Goepfert, J.M., (1974) Alteration of Vascular Permeability in Rabbits by Culture Filtrates of *Bacillus cereus* and Related Species, Infections and Immunity, 10, pp. 299–303.

Glatz, B.A. and Goepfert, J.M. (1977) Production of *Bacillus cereus* Enterotoxin in Defined Media in Fermenter–Grown Cultures, Journal of Food Protection, 40, pp. 472–474.

Granum, P.E. and Nissen, H., (1993) Sphingomyelinase in part of the 'enterotoxin complex' produced by *Bacillus cereus*, FEMS Microbiology Letters, 110, pp. 97–100.

Granum, P.E., Brynestad, S. and Kramer, J.M., (1993) Analysis of enterotoxin production by *Bacillus cereus* from dairy products, food poisoning incidents and non–gastrointestinal infections, International Journal of Food Microbiology, 17, pp. 269–279.

Hames, B.D., and Rickwood, D., Gel Electrophoresis of Proteins a practical approach, IRL Press, Washington, DC.

Harlow, E., and Lane, D., (1988) Antibodies a Laboratory Manual, Cold Spring Harbor Laboratory, Cold Spring Harbor, N.Y. pp. 92–136.

Heinrichs, J.H., Beecher, D.J., Macmillan, J.D. and Zilinskas, B.A., (1993) Molecular Cloning and Characterization of the hblA Gene Encoding the B Component of Hemolysin BL from *Bacillus cereus*, Journal of Bacteriology, 175, pp. 6760–6766.

Kramer, J.M., and Gilbert, R.J., *Bacillus cereus* and Other Bacillus Species, Food Hygiene Laboratory, Central Public Health Library, London, England, pp. 22–70.

Matsudaira, P., (1990) Limited N–Terminal Sequence Analysis, Methods in Enzymology, 182, pp. 602–613.

Ponder, E., (1948) Hemolysis and Related Phenomena, Grune & Stratton, New York.

Stoscheck, C.M., (1990) Quantitation of Protein, Methods in Enzymology, 182, pp. 50–68.

Thompson, N.E., Ketterhagen, M.J., Bergdoll, M.S., and Schantz, E.J., (1984) Isolation and Some Properties of an Enterotoxin Produced by *Bacillus cereus*, Infection and Immunity, 43, pp. 887–894.

Tu, A.T., and Miller, R.A., (1992) Natural Protein Toxins Affecting Cutaneous Microvascular Permeability, J. Toxicol.—Toxin Reviews, 11, pp. 193–239.

Turnbull, P.C.B., *Bacillus cereus* Toxins, F. Dorner and J. Drews (ed.), Pergamon Press, Oxford, pp. 397–448.

Turnbull, P.C.B., Jorgensen, K., Kramer, J.M., Gilbert, R.J. and Parry, J.M., (1979) Severe clinical conditions associated with *Bacillus cereus* and the apparent involvement of exotoxins, Journal of Clinical Pathology, 32, pp. 289–293.

Turnbull, P.C.B., Kramer, J.M., Jorgensen, K., Gilbert, R.J. and Melling, J., (1979) Properties and production characteristics of vomiting, diarrheal and necrotizing toxins of *Bacillus cereus*, American Journal of Clinical Nutrition, 32, pp. 219–228.

Young, J.D.–E., Leong, L.G., DiNome, M.A., and Cohn, Z.A. (1986) A semiautomated Hemolysis Microassay for Membrane Lytic Proteins, Analytical Biochemistry, 154, pp. 649–654.

*Primary Examiner*—James C. Housel
*Assistant Examiner*—Rodney P. Swartz
*Attorney, Agent, or Firm*—DeWitt Ross & Stevens SC

[57] ABSTRACT

The characterization of the protein structure of an enterotoxin to *Bacillus cereus*, designated hemolysin BL, is described herein. A high-yield purification scheme which allows quantitative characterization of the hemolysin BL activity is also described.

5 Claims, 5 Drawing Sheets

BACILLUS CEREUS ENTEROTOXIN AND METHOD OF USE

REFERENCE TO GOVERNMENT GRANT

This invention was made with United States Government support awarded by the USDA, Grant # USDA 93-37201-9194. The United States Government has certain rights in this invention.

FIELD OF THE INVENTION

The present invention is directed to the characterization of the protein structure, designated hemolysin BL, of *Bacillus cereus* and to a high-yield purification scheme which allows quantitative characterization of the hemolysin BL activity.

REFERENCE TO CITATIONS

A full bibliographic citation of the references cited in this application can be found in the section preceding the claims.

DESCRIPTION OF THE PRIOR ART

*Bacillus cereus* (*B. cereus*) is a ubiquitous, usually commensal, soil organism, but it is increasingly being recognized as a potential pathogen, most commonly associated with food poisoning. It produces two distinct food poisoning syndromes, characterized primarily by emesis and diarrhea respectively (Kramer and Gilbert, 1989, Turnbull, 1986). It also causes a variety of nongastrointestinal infections including devastating endophthalmitis, abscess formation, bacteremia, septicemia, cellulitis, endocarditis, meningitis, kidney and urinary tract infections, osteomyelitis, puerperal sepsis and pulmonary and wound infections (Turnbull, 1986).

The molecular nature of the virulence of *B. cereus* is poorly understood. However, the ability to produce dermonecrotic vascular permeability activity correlates with the ability to cause diarrheal food poisoning Turnbull et al., 1979b) and nongastrointestinal *B. cereus* infections (Turnbull et al., 1979a, Turnbull et al., 1979b).

Thompson et al. (1984) described a dermonecrotic enterotoxigenic factor from *B. cereus* B-4ac. This toxin consisted of two or three distinct protein components that were not active individually. The combined components were hemolytic, lethal to mice, cytotoxic to Vero cells, and positive in ileal loop and vascular permeability tests. This toxin was only partially purified so its characterization was incomplete. Bitsaev and Ezepchuk (1987) have also reported a tripartite enterotoxic factor called DL-toxin (Bitsaev and Ezepchuk, 1987).

Beecher and Macmillan (1990, 1991) reported the purification of a tripartite hemolysin, designated hemolysin BL, that was immunologically related to the multicomponent enterotoxin purified by Thompson et al. (1984) and exhibited vascular permeability activity. The hemolysin BL components are designated B, $L_1$, and $L_2$. None of the components has hemolytic or VP activity individually and maximal activity occurs in the presence of all three components. The complete nucleotide sequence of the gene encoding the B component has been determined (Heinrichs et al., 1993).

Isolated B component binds to erythrocytes and sensitizes them to the lytic action of the L components. The L components do not sensitize erythrocytes to lytic action by B, and it is not yet known whether they bind to the cell membrane in the presence or absence of B. When B-sensitized erythrocytes are treated with either $L_1$ or $L_2$ and then washed, the cells lyse upon addition of the third component. Hemolysin BL produces a characteristic and peculiar discontinuous pattern of hemolysis on gel diffusion assays. When components are added together to a well in blood agar, hemolysis does not begin immediately next to the well. Rather, after a period of diffusion, hemolysis begins at some distance (typically several millimeters) from the well edge, forming a ring around the well. With time, cells within the ring are completely lysed but hemolysis does not occur much beyond the initial diameter of the ring. Hemolysin BL was previously purified by anion exchange chromatography and preparative electrophoresis, using monoclonal antibodies to detect B and $L_2$. The yield was very low and only qualitative determinations of hemolytic and VP activities were possible.

There are currently two commercial immunoassays available for the detection of the diarrheal enterotoxin of *B. cereus*; the Bacillus Diarrhoeal Enterotoxin (BDE) Visual Immunoassay from Tecra, and the *B. cereus* Enterotoxin-Reverse Passive Latex Agglutination (BCET-RPLA TD950) kit from Oxoid. Both kits are in general use (Buchanan and Schultz, 1992; Carlson et al, 1994; Granum et al, 1993). However, the value of these kits is questionable because the diarrheal enterotoxin has now been identified as a three-component structure. Further confusing the issue, these kits detect different antigens (Christiansson, 1993).

SUMMARY OF THE INVENTION

The present invention is directed to a substantially pure protein composition "B" isolatable from *Bacillus cereus* and having the following properties: a) isoelectric point: 5.34; b) molecular weight (kD): 37,800; c) N-terminal sequence: S-E-I-E-Q-T-N-N-G-T-A-L [SEQ. ID. NO. 1]; d) extinction coefficient at 280nm, 1 cm path length: 1.32.

The present invention is also directed to a substantially pure protein composition "$L_1$" isolatable from *Bacillus cereus* and having the following properties: a) isoelectric point: 5.33; b) molecular weight (kD): 38,500; c) N-terminal sequence: x-E-T-I-A-Q-E-Q-K-V-G-N-Y-A-L-G-P-E, where x is undetermined [SEQ. ID. NO. 2]; d) extinction coefficient at 280nm, 1 cm path length: 1.85.

The present invention is further directed to a substantially pure protein composition "$L_2$" isolatable from *Bacillus cereus* and having the following properties: a) isoelectric point: 5.33; b) molecular weight (kD): 43,200; c) N-terminal sequence: E-T-Q-x-E-N-M-D-I-x-S, where x is undetermined [SEQ. ID. NO. 3], where x is undetermined; d) extinction coefficient at 280nm, 1 cm path length: 0.83.

The present invention is also directed to a substantially pure enterotoxin of *Bacillus cereus* comprising the following protein compositions having the following properties: (B): a) isoelectric point: 5.33; b) molecular weight (kD): 38,500; c) N-terminal sequence: S-E-I-E-Q-T-N-N-G-T-A-L [SEQ. ID. NO. 1]; d) extinction coefficient at 280nm, 1 cm path length: 1.32; ($L_1$): a) isoelectric point: 5.33; b) molecular weight (kD) : 38,500; c) N-terminal sequence: x-E-T-I-A-Q-E-Q-K-V-G-N-Y-A-L-G-P-E, where x is undetermined [SEQ. ID. NO. 2]; d) extinction coefficient at 280nm, 1 cm path length: 1.85; ($L_2$) : a) isoelectric point: 5.33; b) molecular weight (kD) : 43,200; c) N-terminal sequence: E-T-Q-x-E-N-M-D-I-x-S, where x is undetermined [SEQ. ID. NO. 3]; d) extinction coefficient at 280nm, 11 cm path length: 0.83.

The present invention is also directed to a bioreagent suitable for antibody assays comprising a substantially pure protein composition having the properties expressed in the previous paragraph.

The present invention is further directed to an antibody specific to the enterotoxin hemolysin BL.

Further, the present invention is directed to an antibody specific to hemolysin BL, said antibody being characterized in that it reacts with at least one of the three component proteins B, $L_1$ or $L_2$ of hemolysin BL.

The present invention is further directed to a diagnostic kit for assaying the presence of hemolysin BL comprising the antibody described above in one or more containers and directions for its use.

The present invention is also directed to an immunoassay method for the detection of hemolysin BL, which comprises: contacting a sample suspected of containing hemolysin BL with an antibody that is specific to hemolysin BL in order to form an immune complex, and determining the presence of the complex in order to detect hemolysin BL in the sample.

Further, the present invention is directed to a process for isolating protein components of hemolysin BL from *Bacillus cereus* cells, comprising:

a. cultivating *Bacillus cereus* cells in an enriched medium containing the nutritional substances necessary to grow and support the cells;
b. separating the cells from the medium;
c. concentrating the cells; and
d. separating the protein components.

Further still, the present invention is directed to an improved process for isolating protein components of hemolysin BL from *Bacillus cereus* cells, the improvement comprising separating the protein components by hydroxylapatite chromatography.

The high-yield purification scheme which was developed in the present invention, allows quantitative characterization of hemolysin BL activity and determination of the molecular weight (MW), isoelectric point (pI), N-terminal sequence of each component, and extinction coefficients. Milligram quantities of the B, $L_1$, and $L_2$ components were highly purified by a combination of anion exchange and hydroxylapatite chromatography.

A description of "extinction coefficient" is as follows: the amount that a protein absorbs at 280nm is a function of the tryptophan and tyrosine residues present. Thus, the extinction coefficient (E) is an indicator of the protein composition with respect to these two amino acids. As used herein, the term "extinction coefficient" or "E" is defined as the absorbance of 280nm of a 1 mg/ml protein solution through a 1 cm path length. To obtain the concentration of a protein, the absorbance at 280nm ($A_{280}$) is divided by E for that protein. Reference is made to Stoscheck (1990), which is incorporated herein by reference, for an description of the determination of extinction coefficients.

The purification process of the present invention advantageously separates and purifies the three components in hemolysin BL.

With this high-level separation, the hemolytic and vascular permeability (VP) activities of this toxin were characterized quantitatively. A dermonecrotic VP factor is believed to be a virulence factor in such illnesses as diarrheal food poisoning as well as a variety of mild to severe infections.

Estimation of the physical characteristics of the components is also improved, and the amino-terminal sequence can now be determined for each component. Turbidimetric hemolysis assays of the toxin exhibits a highly unusual dose response "zone phenomenon" that provides a tentative model for the mechanism of the discontinuous hemolytic pattern produced in blood agar. Hemolysin BL produced by the purification process of the present invention produced a severe dermonecrotic reaction that had not previously been observed. In addition, hemolysin BL is a diarrheal enterotoxin and may also be a major virulence factor in other nongastrointestinal infections.

The combined components had VP activity at low doses and were necrotic at higher doses. The toxin exhibited an unusual dose response "zone phenomenon" in turbidimetric hemolysis assays. Activity increased up to 200 ng/ml, then decreased to 350 ng/ml, and was constant up to at least 2500 ng/ml. This behavior may provide an explanation for the unusual discontinuous pattern typical of hemolysin BL in gel diffusion assays. At high concentrations of one or two components the presence of low amounts of the complementary component(s) resulted in full hemolytic activity. Erythrocytes were protected from lysis by $Zn^{++}$ at micromolar concentrations but not by $Ca^{++}$ and $Mg^{++}$ up to 25 mM. These data provide guidelines for future work on this toxin and indicate that hemolysin BL is the dermonecrotic vascular permeability factor implicated as a *B. cereus* virulence factor.

The present invention is specifically useful to both regulatory agencies and food industries and analytical laboratories in monitoring safety of food products carrying out epidemiologic studies, and managing food poisoning caused by *B. cereus*.

Other objects and advantages of the invention will be apparent from the following detailed description and figures setting forth the preferred embodiment of the invention.

DESCRIPTION OF THE DRAWINGS

FIG. 1 and 2.) (B) The column was loaded with pooled fractions from the DE-52 column determined to contain the $L_1$ and $L_2$ components of hemolysin BL (fractions 9 to 15; FIG. 1 and 2).

FIG. 5 is a graph illustrating dose-response curves in turbidimetric hemolysis assays for combined and individual components of hemolysin BL in Experiment 4. The curves were obtained by varying the concentration of one or more components. The values along each x-axis represent the final concentration of the individual components that vary in that experiment. A: All three components were combined and the mixture was diluted to the indicated concentrations. B symbols: ●, the B component was held at 1000 ng/ml and each L component varied as indicated. ■, both L components were held at 1000 ng/ml and B varied as indicated. C symbols: ●, B and $L_2$ were each held at 1000 ng/ml and $L_1$ varied as indicated. ■, B and $L_1$ were held at 1000 ng/ml and $L_2$ varied as indicated. ●, B was held at 100 ng/ml and $L_1$ and $L_2$ each varied as indicated. ■, $L_1$ and $L_2$ were each held at 100 ng/ml and B varied as indicated. Hemolysis activity was determined after 1 h 15 min for experiment A and 1 h 30 min for the other experiments.

DETAILED DESCRIPTION OF THE INVENTION

AMINO ACIDS

The amino acids are shown either by three letter or one letter abbreviations as follows:

| Abbreviated Designation | Amino Acid |
|---|---|
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

HEMOLYSIN BL

The present invention provides a process of isolating and purifying protein components of a *B. cereus* enterotoxin called hemolysin BL. This toxin is composed of three distinct proteins, designated B, $L_1$ and $L_2$ with respective sizes of 37.7, 38.5 and 43.2 kDa and pIs of 5.34, 5.33 and 5.33. The N-terminal amino acid sequences have been determined and are listed in Table 1, infra.

Hemolysin BL is a tripartite toxin with potent hemolytic, cytotoxic, dermonecrotic, and vascular permeability activities. The individual components do not exhibit toxic activity individually, and maximal activity requires all three components. Hemolysin BL is lytic in varying degrees to erythrocytes from different species, toxic to Chinese hamster ovary cells in culture, and retinal tissue in vitro and in vivo.

Hemolysin BL causes vascular permeability (VP) and dermonecrosis in rabbit skin, and fluid accumulation in rabbit ileal loops, which establishes hemolysin BL as a diarrheal enterotoxin.

PRODUCTION AND PURIFICATION OF ENTEROTOXIN/HEMOLYSIN BL

The present invention is directed specifically to a simple, gentle, high yield method of purifying the components of the tripartite hemolysin, designated hemolysin BL, which does not require access to specific antibodies. This purification scheme enables the improvement of the characterization of the individual hemolysin BL components.

The purification scheme provides ample antigen for antibody production, which allows development of specific hemolysin BL detection methods. Highly specific polyclonal and monoclonal antibodies have been produced and used to develop rapid and specific immunoassays for hemolysin BL.

The three components in hemolysin BL can be highly purified by a high-yield combination of anion exchange and hydroxylapatite chromatography. The present invention demonstrates a straightforward, high yield, chromatographic method for the purification of all three components.

Growth medium:

The enterotoxin/hemolysin BL is secreted from *B. cereus* cells in the mid to late log growth phase. The cells are grown in an appropriate medium known to the art for providing sufficient nutrients to allow rapid growth and toxin secretion. The most commonly used medium for toxin production in *B. cereus* is brain heart infusion broth supplemented with 0.1% glucose (BHIG). Other media may be adapted for the purpose as well. These include any rich liquid media that promote rapid growth such as, but not limited, to standard formulations of nutrient broth, Trypticase soy broth and beef extract. The media may be modified from the standard formula to enhance toxin production, e.g. by the addition of a useable carbohydrate such as glucose.

The preferred medium for the present invention is caseamino acids/glucose/yeast extract (CGY) broth. It is a modification of a medium described by Glatz and Goepfert (1977) and consists of 2% caseamino acids, 0.4% glucose, 0.6% yeast extract, 0.2% $(NH4)_2SO_4$, 1.4% $K_2HPO_4$, 0.6% $KH_2PO_4$, 0.1% Na citrate, and 0.2% $MgSO_4$ (Beecher and Wong, 1994). This medium is preferred over BHIG because it promotes similarly high toxin production levels, but contains less heterogeneous colored components, which complicate subsequent purification procedures.

Growth parameters and bacterial strain:

Growth conditions can be varied depending on the specific goals of the worker. Generally the goal is to maximize toxin production and minimize toxin degradation. Specific optimal parameters, which vary with the bacterial strain used for toxin production, may be empirically determined. The method of inoculation of the production batch will generally be standardized to minimize batch to batch variation.

The toxin may be grown as a stationary or aerated culture, in flasks or other containers, or in fermenters. Toxin production can be monitored by bioassay or immunoassay if antibodies are available. Relevant bioassays include, but are not limited to, the ligated rabbit ileal loop test, the rabbit vascular permeability (VP) test, and the discontinuous hemolysis assay of Beecher and Wong (1994).

Toxin production varies from one *B. cereus* strain to another. Any strain that produces sufficient amounts of toxin to suit the workers' needs may be used. For the present invention, the preferred bacterial strain is *B. cereus* F837/76, which produces high levels of hemolysin BL and relatively low levels of other hemolysins and enzymes, such as proteases.

The preferred inoculation method is the addition of an overnight active stationary culture of the bacterium, usually in the same culture medium as the production medium. The preferred inoculum size is 0.5 to 1% of the volume of the production culture. The preferred growth parameters are as follows: 5 to 6 hours at 32° C., 200 rpm on a rotary shaker, in flasks containing medium at one forth to one fifth the maximum volume of the flask.

Harvest of toxin:

Toxin harvest involves separation of cells from the culture supernatant. This may be done in any way practicable, including filtration or precipitation. The preferred method for this invention is centrifugation. The culture is centrifuged at 8,000× g for 10 to 20 min, the supernatant collected, and the pellet of cells discarded. Prior to centrifugation, ethylenediaminetetraacetic (EDTA) is added to a concentration of 1 mM to inhibit the major protease of *B. cereus* F837/76 and minimize proteolytic degradation of hemolysin BL. Other protease inhibitors may be needed for other bacterial strains if they produce different proteases. Batch sizes range from 1 to 8 liters, but may be scaled up or down as needed.

Concentration of toxin:

The toxin generally must be concentrated to a volume that is convenient to handle in subsequent purification steps. This may be done by any means known to the art and practicable, including, but not limited to, 1) ultrafiltration, 2) adsorption to an appropriate matrix such as an ion exchanger or hydroxylapatite followed by desorption with an appropriate buffer, 3) precipitation with an appropriate solvent or salt, followed by collection of precipitate and solubilization of proteins in a minimum volume. Adsorption and precipitation methods may be varied such that a primary separation of hemolysin BL proteins from some other proteins is effected. The preferred method for this invention is precipitation with 80 to 85% ammonium sulfate at 0° to 4° C. for greater than 2 h. The precipitate is collected by centrifugation at 8,000× g, for 30 min. Proteins are solubilized with a minimum volume of water.

Preparation of toxin concentrate:

The toxin concentrate may have to be prepared for the subsequent purification step. The specific preparation will vary, depending on the first purification step chosen and will generally involve changing the buffer in which the toxin is solubilized. This may be done by dialysis or gel filtration or dilution into the desired buffer. For this invention, the preferred preparation is overnight dialysis of the concentrate at 4° C. against 100 to 200 volumes of 25 mM bis-Tris-HCl, 1 mM EDTA, pH 5.9, with two buffer changes.

Purification of hemolysin BL components:

Purification of the hemolysin BL components may include any combination of methods that result in the separation to substantial purity of each or any individual component from the other components and other non-hemolysin BL proteins. Potentially useful methods include, but are not limited to 1) column chromatography, including ion exchange chromatography, and chromatofocusing (a form of ion exchange chromatography in which proteins elute from the column near their isoelectric points), 2) hydroxylapatite chromatography, 3) gel filtration chromatography, 4) isoelectric focusing, 5) preparative electrophoresis, 6) gel filtration chromatography, which allows limited protein load for optimal resolution and permits only poor resolution of proteins in the size range of the hemolysin BL components and the many other proteins within that range, 7) isoelectric focusing, which allows limited protein load and yield and presents numerous technical difficulties in its performance, and 8) preparative electrophoresis, which allows low protein load and yield.

Column chromatography using adsorptive matrices is preferred for this invention because of the high resolution, high load capacities and yields, and great variation of column sizes allowed by these methods.

Anion exchange chromatography is preferred over cation exchange chromatography because the pH required to bind the proteins comprising hemolysin BL is 4 or lower, which is detrimental to the stability of the components. Proteins bind to ion exchangers as a function of the surface charge of each at a given pH. Usually proteins bind to anion exchangers one pH unit above their pIs and to cation exchangers one pH unit below their pIs.

Hydroxylapatite (HA) chromatography is preferred for this invention because of unexpectedly and unusually good resolution of the components from one another. Proteins bind to HA as a function of surface properties (largely surface charge). The hemolysin BL components elute from HA in an order unpredictable from their isoelectric points and behavior on anion exchangers. $L_1$ and $L_2$ closely coelute from anion exchangers but may be well resolved from one another upon elution from HA. The B component, which behaves on anion exchangers as if it has a more acidic surface than the L components, elutes very late from HA. The elution of B with the relatively high phosphate concentration of around 120 mM is suggestive of a neutral surface charge (pI 6 to 7) or of specific interaction with phosphate.

The preferred mode of elution of hemolysin BL components is with linear gradients of NaCl or phosphate from anion exchangers and HA respectively. Other methods may be used, such as step gradients of NaCl and phosphate, or pH change, but resolution will be sacrificed.

The purification (chromatographic) steps may be applied in any order that results in substantially pure preparations of the components of hemolysin BL. The preferred sequence for this invention is 1) anion exchange chromatography, 2) HA chromatography and 3) anion exchange chromatography.

Step 1 results in separation of component B from the two L components and minimal separation of $L_1$ from $L_2$. Fractions containing the proteins of interest are identified by the methods described below and appropriate fractions are applied directly to the HA column. Usually, two pools of fractions containing respectively 1) B and 2) $L_1$ plus $L_2$ are separately applied to and eluted from a HA column. The fractions from step 1 (anion exchange) are applied directly to the HA column in step 2 without a change in the buffer composition of the samples. Ideally, only three chromatographic columns (one anion exchange and two HA columns) are needed to complete steps 1 and 2, with no manipulation of sample buffer composition between the steps.

If the steps are reversed, i.e., HA first, followed by anion exchange, the hemolysin BL components will not bind directly to the anion exchanger after elution from HA. The pooled samples must be placed by dialysis or gel filtration into the anion exchange binding buffer, which adds a manipulation step compared with the preferred sequence. If HA is used as step 1, the three hemolysin BL components will separate from one another, necessitating the collection of a minimum of three sample pools for step two. At minimum the HA followed by anion exchange sequence will result in one HA column and three anion exchange columns. The actual number of column runs needed to produce substantially pure hemolysin BL components will vary depending on the column sizes and protein loads used. Overloading of columns results in decreased resolution. A remedy for a given amount of protein on a given column is to apply less per column run, e.g. apply portions of sample pools, or collect multiple small sample pools.

The third chromatographic step is a second anion exchange column. This step is included as a high resolution step to remove low level contaminants of other hemolysin BL components and other proteins from the component preparations. The step requires a change of buffer to the anion exchange binding buffer described above and below. This step is performed on a small column that allows highly reproducible separations of high resolution. Protein loads are determined by the capacity and resolving power of the column to be used. This step is optional and may be omitted if the preparations from step two are of sufficient purity to suit the specific needs of the worker.

Identification of proteins comprising hemolysin BL:

Hemolysin BL components in the chromatographic fraction may be identified by their respective activities, or by immunoassay if antibodies are available. The preferred method for this invention is the gel diffusion hemolysis assay described below, coupled with identification of proteins of specific sizes on SDS-PAGE gels.

BIOREAGENTS

The protein components of hemolysin BL can be isolated for use as bioreagents and used to prepare polyclonal and monoclonal antibodies for detection of the hemolysin BL enterotoxin. The antibodies can be used in test kits which are used to diagnose clinically suspected contamination of hemolysin BL. The proteins can be recognized and distinguished from other proteins according to the characteristics determined in the experiments below.

PRODUCTION OF ANTIBODIES TO HEMOLYSIN BL

Antibodies can be prepared according to methods known to the art. Polyclonal antibodies can be produced by injecting electrophoresis gel slices containing separated hemolysin BL components into rabbits essentially as described by Harlow and Lane (1988). Antisera to all three hemolysin components react with a single major band from B. cereus culture supernatants on Western immunoblots and will exhibit reactions of nonidentity with each other in double immunodiffusion assays.

Hemolysin BL proteins can also be employed to produce monoclonal antibodies to the proteins utilizing the procedure described by Fazekus et al. (1980). The essential steps are as follows:
1. immunize an animal, preferably a rodent such as a rat or mouse, or a rabbit, with the protein component;
2. isolate β-lymphocytes, suitably spleen lymphocytes, from the immunized animal;
3. fuse the isolated β-lymphocytes with myeloma cells from an animal, preferably a rodent such as a rat or mouse;
4. select from the fused cells those hybridoma cell lines which react positively with the proteins;
5. clone the hybridoma cells to produce additional monoclonal antibodies.

In general overview, polyclonal and monoclonal antibodies (referenced herein as "antibodies" unless otherwise specified) specific for hemolysin BL can be produced by immunizing BALB/c mice with hemolysin BL. Spleen cells from the mice so immunized are fused with a mouse myeloma cell, with the fusion being effected with treatment in polyethylene glycol in accordance with known methods. The resulting hybridomas are cultured and then selected for antibody activity. The cells producing antibodies specific to hemolysin BL are detected by means of an ELISA in the manner well known to the art. The antibody is purified from ascites fluid in conventional ways. The cloned cell line so created and selected is perpetuated by conventional cell culturing techniques.

Any of a large number of clinical tests may be employed utilizing the antibodies of this invention. Typical tests include radioimmunoassay, enzyme-linked-immunoassay (ELISA), precipitation, agglutination, direct and indirect immunofluorescence and complement fixation. These tests may employ competitive and sandwich-type assays.

The antibodies are tested for specificity by ELISAs and by immunoblotting of a variety of enterics. By these means, it can be determined that the antibody forms a strong reaction by direct ELISA with hemolysin BL.

ELISAs are a conventional method for assaying for the presence of an antigen in a sample of test material. The sandwich ELISA of the invention is adapted to assay for the presence of hemolysin BL in a sample of test material and includes the following steps. First, a known antibody to hemolysin BL is bound to a suitable adsorbtor substrate. Preferably, a plastic culture plate is used, such as a 96-well polystyrene culture plate (Costar, Cambridge, Mass.—Model No. 3596). A solution of antibody to hemolysin BL is placed in each of the wells and allowed to remain under conditions such that the antibody to hemolysin BL is adsorbed to the surface of the wells. Unadsorbed antibody solution is then washed away, leaving the antibody to hemolysin BL bound to the adsorptive walls of the wells, which shall be referred to as "adsorbtor substrate units." With antibody to hemolysin BL adsorbed to them, they shall be referred to as "antibody to hemolysin BL substrate units." The antibody to hemolysin BL substrate units is then treated with an appropriate blocking reagent, such as nonfat dried milk, to block non-specific binding sites. After appropriate incubation, this reagent is removed.

Next, a known quantity of the test material is exposed to the antibody to hemolysin BL-charged substrate units for an appropriate period of time, and then is removed by washing. Any hemolysin BL in the test material will bind to the antibody to charged substrate units.

Similarly, a standard preparation of hemolysin BL is exposed to another set of antibodies to hemolysin BL-charged substrate units to serve as a control.

The antibody referred to above is added to the antibody to hemolysin BL-charged substrate units to bind with any bound hemolysin BL. After appropriate incubation, the unbound antibody is removed by washing.

The antibody to hemolysin BL-charged substrate units are reacted with test samples of hemolysin BL and are then assayed for the presence of the antibody.

Preferably this is done by exposing antibody to hemolysin BL-charged substrate units reacted with the test samples or hemolysin BL and the antibody thereon to a marker-coupled anti-mouse antibody to allow the marker-coupled antibody to bind to any antibody present. The unbound marker-coupled antibody is then removed, and the amount of marker remaining on the antibody to hemolysin BL-charged substrate units is measured. The marker may be an enzyme measured by its effect on a selected reagent, a fluorescent material, a radioactive material, or any other of the markers familiar to one skilled in the art. It will be apparent that the antibody itself may be combined directly with a marker, whereupon the step of reacting a marker-coupled anti-mouse antibody may be omitted.

The antibody may also be used in other conventional ELISAs. For example, a sample of test material may be bound to an adsorbtor substrate and then exposed to the antibody disclosed above. The antibody binds to any hemolysin BL present in the test material. Unbound portions of the antibody are then removed. Next, an assay comparable to those discussed above is conducted for the presence of bound antibody.

The antibody of the present invention may also be used in any of the generally known methods of using such antibodies in immunohistological techniques for examining a substantially cohesive, nonfluid test material, such as a cell or tissue sample. Preferably, the sample is a food product or a fecal sample or an extract of the same. The test material is incubated with the antibody to bind the antibody to hemolysin BL present in the test material. The test material is then washed to remove the unbound portion of the antibody. The antibody may then be reacted in such a way as to make its presence visually apparent. Typically, the test material bearing antibody bound to hemolysin BL contained therein is incubated with a marker-labeled anti-mouse antibody comparable to those discussed above. The marker-labeled antibody binds to the antibody. A marker is selected such that it may be made visually apparent. Fluorescent and enzyme markers typically are used. The test material is then microscopically observed under conditions adapted to render the marker visually perceivable. The antibody to hemolysin BL is specifically useful as a reagent for the rapid detection of hemolysin BL in food and clinical specimens.

The present invention also includes kits, e.g., diagnostic assay kits, for utilizing the antibody to hemolysin BL and carrying out the method disclosed above. In one embodiment, the diagnostic kit would conventionally include the antibody to the hemolysin BL in one or more containers, a conjugate of a specific binding partner for the antibody, a label capable of producing a detectable signal, and instructions for its use. The antibody can be a polyclonal antibody, a monoclonal antibody, a mixture of polyclonal antibodies, a mixture of monoclonal antibodies, and a mixture of polyclonal and monoclonal antibodies. The kit may be conjugated to a label, as is well known to the art. Various labels include enzymes, radioisotopes, particulate labels, chromogens, fluorescers, chemiluminescers, coenzymes, free radicals, and bacteriophages. Additionally the antibody may be bound to a support.

The instructions for use are suitable to enable an end user to carry out the desired test. By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like. It is within the scope of this invention to provide manual test kits or test kits for use in automated analyzers.

A specific diagnostic kit could be in a dipstick format. This could involve adsorbing polyclonal immunoglobulin to a hydrophobic polyvinylidene difluoride (PVDF)-based membrane. The PVDF membrane is then treated with 5% bovine serum albumin to block nonspecific binding sites. The PVDF membrane is dipped for 30 minutes in an enrichment culture of food that may contain hemolysin BL. After washing, the PVDF membrane is treated with the antibody. This antibody will bind to any hemolysin BL cells bound to the PVDF membrane. The bound antibody is detected with alkaline phosphatase-conjugated goat anti-mouse immunoglobulin that reacts with Nitro blue tetrazolium/5-bromo-4-chloro-3-indolylphosphate substrate to produce purple spots as a positive reaction.

Each of the protein components B, $L_1$ and $L_2$ can also be isolated by the purification method described herein as a bioreagent and used to prepare antibodies for detection of hemolysin BL in a sample. The antibodies can be provided in test kits which are used to diagnose cases of suspected hemolysin contamination.

The examples below provide specific examples of the invention disclosed herein.

EXAMPLES

The following examples are presented to illustrate the advantages of the present invention and to assist one of ordinary skill in making and using the same. The examples are not intended in any way to otherwise limit the scope of the disclosure or protection granted by the patent.

Experiment 1
Purification of Hemolysin BL Culture Medium

The culture medium used for the production of hemolysin BL was a modification of one described by Glatz and Goepfert (1977). It consists of 2% caseamino acids, 0.4% glucose, 0.6% yeast extract, 0.2% $(NH_4)_2SO_4$, 1.4% K2HPO$_4$, 0.6% $KH_2PO_4$, 0.1% Na citrate, and 0.2% $MgSO_4$. We have found that levels of hemolysin BL produced in this medium (termed "CGY") are comparable to those attained in brain heart infusion broth supplemented with 0.1% glucose (BHIG), which is the most commonly used medium for *B. cereus* toxin production. However, CGY contains much lower levels of colored contaminants, making purification easier than with BHIG.

Production of hemolysin BL:

Production of hemolysin BL from *B. cereus* F837/76 was as described previously (Beecher and Macmillan, 1990), except that cultures were grown at 32° C. instead of 37° C. and EDTA (1 mM) was added at the time of harvest (5 h) to inhibit proteolysis. Four liters of culture supernatant was concentrated with 90% saturated $(NH_4)_2SO_4$, resuspended in 50 ml of water, and dialyzed overnight at 40° C. against 2 liters of 25 mM Bis-Tris-HCl, 1 mM EDTA, pH 5.9, with two buffer changes.

Chromatography:

Whatman DE-52 was charged with counter ions with 0.25 M Bis-Tris-HCl, pH 5.9, and packed into a 2.6 cm diameter column to a height of 9 cm. The column was equilibrated with 25 mM Bis-Tris-HCl, pH 5.9, at a flow rate of 3 ml/min. The sample was dialyzed against the equilibration buffer plus 1 mM EDTA prior to application to the anion exchanger.

Proteins were eluted with a linear gradient of NaCl from 0 to 0.5 M over 400 ml and collected in 6-ml fractions. Hydroxylapatite (HA) chromatography was performed using a 1.6 by 6.4 cm column of Bio-Gel® HTP (BioRad, Richmond, Calif.) equilibrated with 10 mM NaCl. Selected fractions from the DE-52 column were pooled and applied directly to the HA column at a flow rate of 1.5 ml/min. Proteins were eluted into 2.5 ml fractions with a linear gradient of sodium phosphate buffer, pH 6.8, from 0 to 0.24 M over 120 ml.

To concentrate proteins from HA chromatography, pooled fractions were dialyzed against 25 mM Bis-Tris-HCl, pH 5.9, and applied to a Mono-Q (MQ) HR 5/5 anion exchange column (0.5 by 5 cm, Pharmacia) equilibrated with the same buffer. Proteins were eluted with a linear gradient of NaCl from 0 to 0.25 M over 40 ml at a flow rate of 1 ml/min. This step also served as a high-resolution anion exchange step that removed minor contaminating proteins.

Electrophoresis and protein blotting:

Sodium dodecyl sulfate polyacrylamide gel electrophoresis (SDS-PAGE) with buffer formulations of Hames (1981) were run in a Mini Protean II dual slab cell (BioRad).

The minigels were either silver-stained by the method of Blum et al. (1987) or used for protein blotting. Proteins resolved in SDS-PAGE gels were transferred to polyvinylidine difluoride (PVDF) membranes (Millipore, Bedford, Mass.) in a Mini Trans-BlotR electrophoretic transfer cell (BioRad) at 100 V constant voltage for 1 h 15 min. Isoelectric points were determined on a PhastSystem (Pharmacia, Piscataway, N.J.) using Pharmacia IEF standards and PhastgelR IEF gels with a pH range of 4 to 6.5.

Results:

Reference is made to FIG. 1, which represents the elution profile of *B. cereus* proteins from the DE-52 anion exchange column. The discontinuous lytic pattern typical of hemolysin BL in gel diffusion assays was produced directly by fractions 20 to 40. Production of the discontinuous pattern indicates the presence of all three hemolysin BL components. On previous DE-52 columns (Beecher and Macmillan, 1991) the B component was well separated from the L components indicating that the activity seen in these fractions was the result of tailing of small concentrations of the L components into the peak fractions of the B component.

Fractions containing the L components did not possess discontinuous hemolytic activity and were located by complementation with the B component. Partially purified preparations of B that still possessed discontinuous hemolytic activity could be used for detection of L activity. A lytic zone eventually developed between the wells and beyond the hemolytic zone of the B-containing fractions.

Some of the fractions containing L components possessed continuous type hemolytic activity, i.e., lysis began at the well edge and proceeded outward. We do not yet know if this activity is due to a different hemolysin, the combination of sphingomyelinase and lecithinase (Gilmore et al., 1989), or the combination of L components with other *B. cereus* metabolites.

Figure 1:
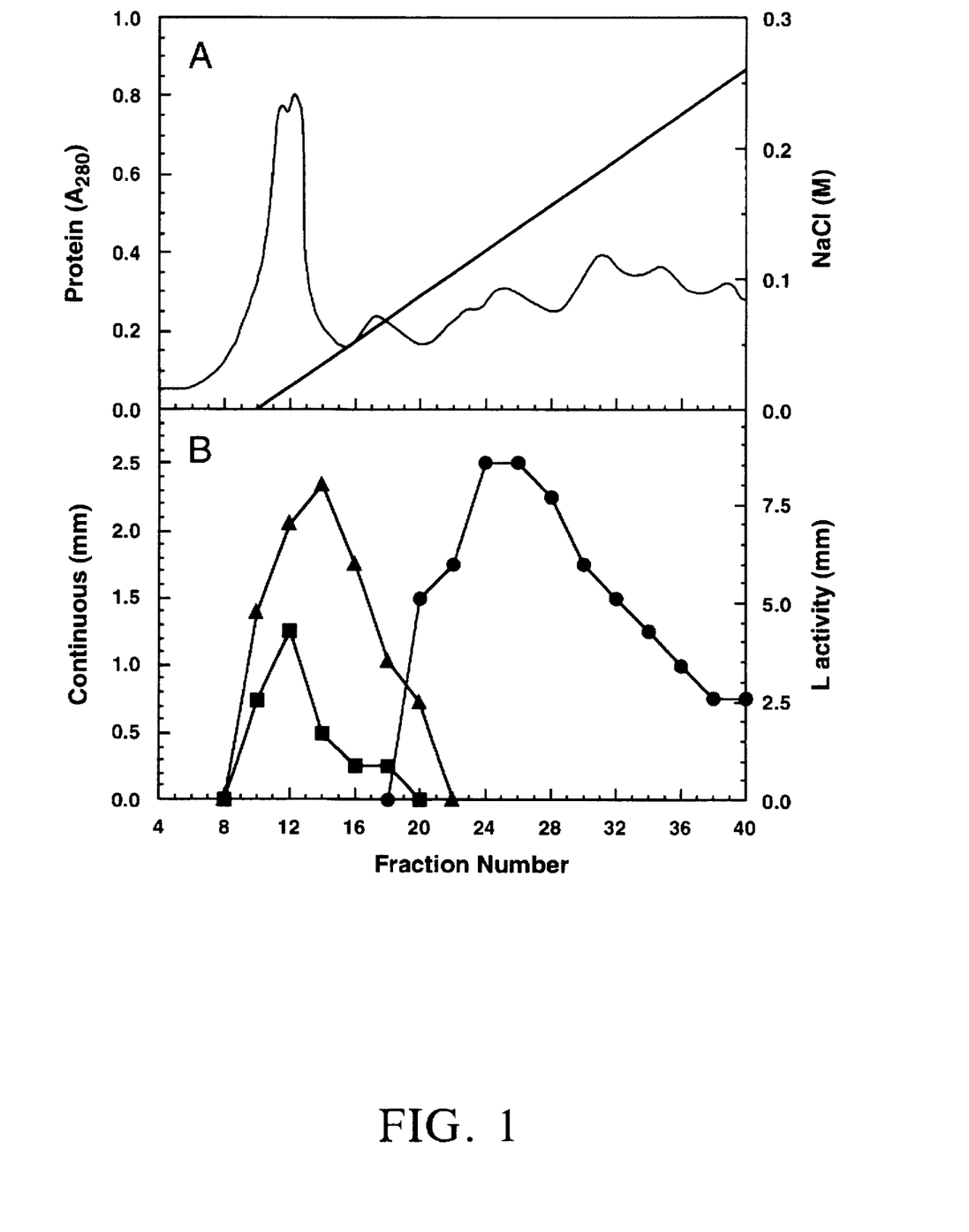
FIG. 1 is an elution profile of hemolysin BL components from DE-52 column in Experiment 1. (A) NaCl gradient and elution of protein as measured by $A_{280}$; (B) discontinuous (●) and continuous (■) hemolysis activity in gel diffusion assay. L activity (▲) was determined in the gel diffusion assay by complementation with B.
Figure 2:
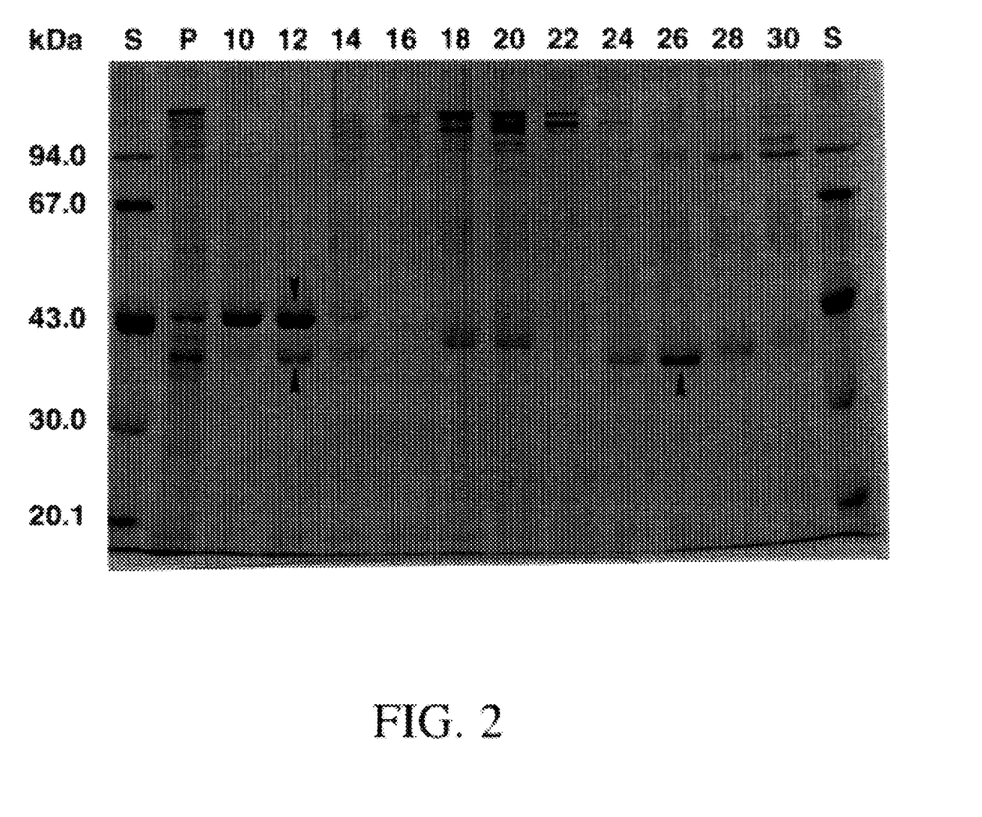
FIG. 2 is an SDS-PAGE of fractions from DE-52 chromatography in Experiment 1. Lanes: S, Pharmacia low-molecular-weight standards (sizes indicated on the left); P, ammonium sulfate-precipitated proteins from culture supernatant of *B. cereus* F837/76. The numbers at the top of the other lanes correspond to the fraction numbers from the DE-52 column in FIG. 1. The top arrow in lane 12 points to $L_2$, the bottom arrow points to $L_1$, and the arrow in lane 26 points to B.
Figure 3:
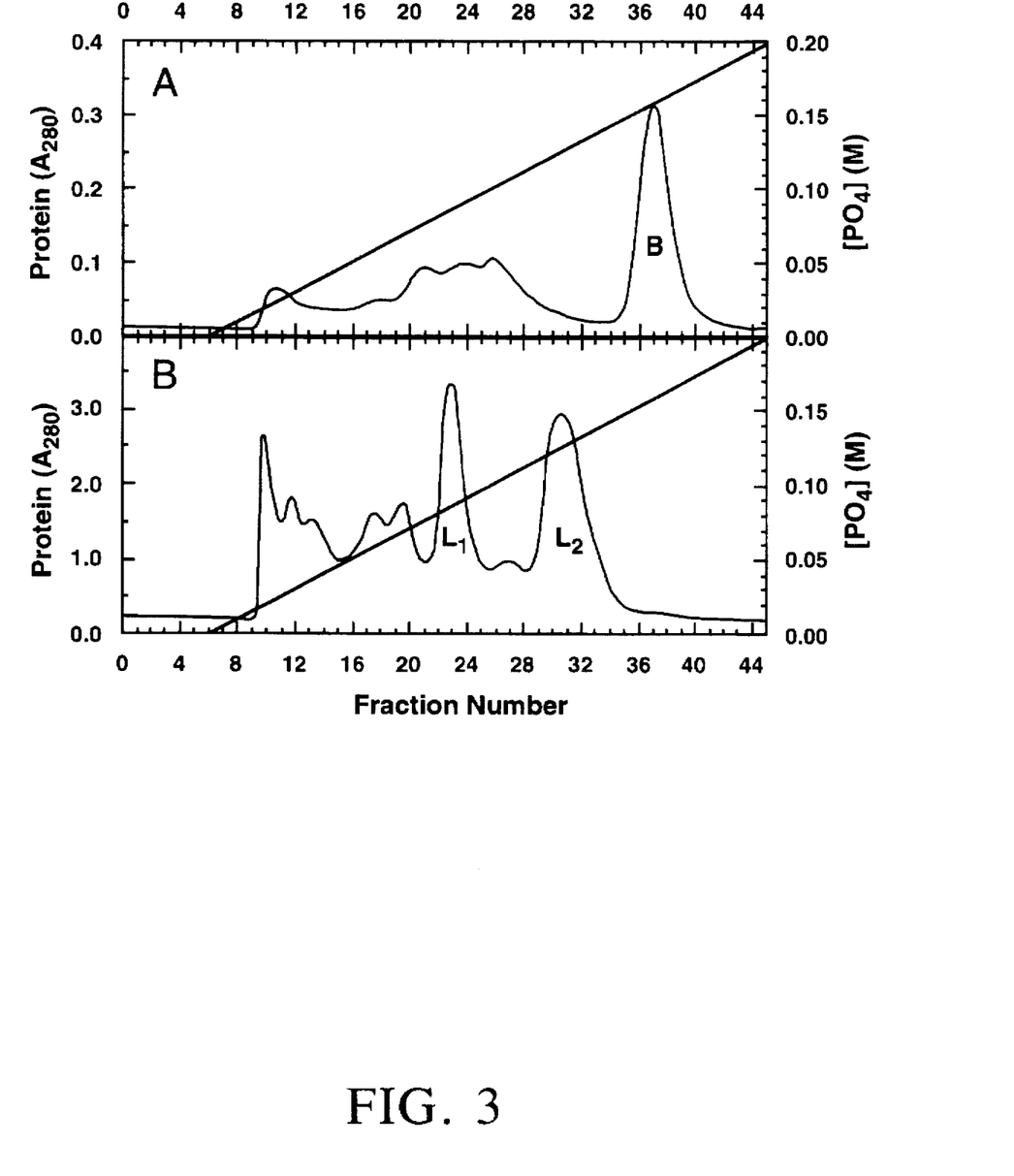
FIG. 3 are elution profiles of hemolysin BL components from an HA column in Experiment 1. (A) The column was loaded with pooled fractions from DE-52 column determined to contain the B component of hemolysin BL (fractions 24 to 29.
Figure 4:
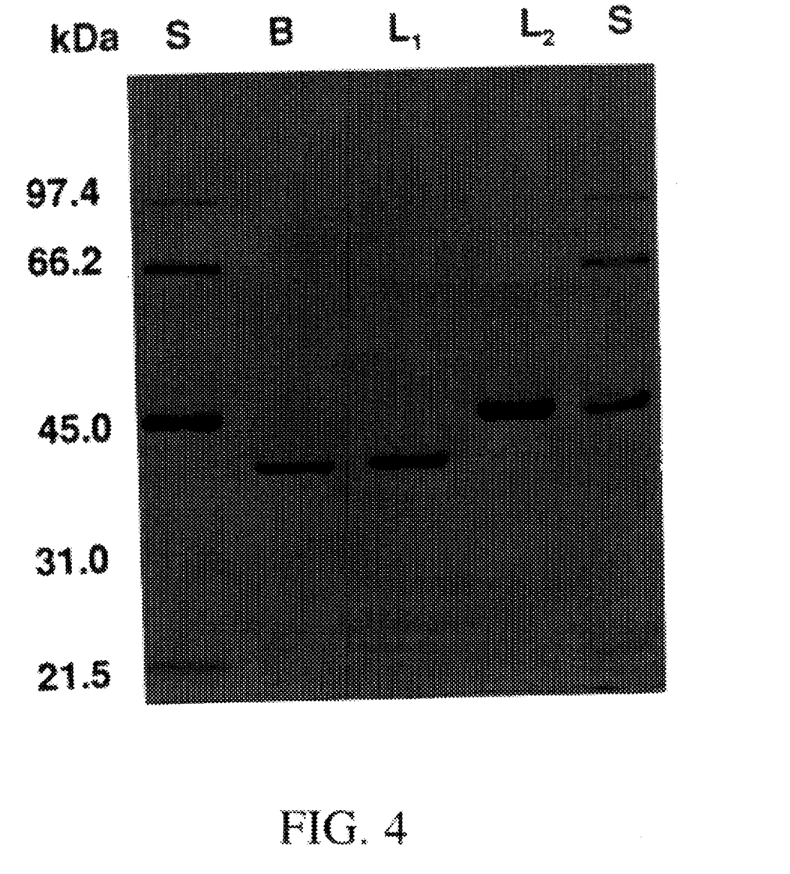
FIG. 4 is an SDS-PAGE of purified hemolysin BL components. Proteins were eluted from a Mono-Q column. Lane S indicates the Pharmacia low-molecular-weight standards (sizes shown on left). The other lanes are labeled with the designations assigned to the respective components of hemolysin BL. The sample lanes were loaded with 200 ng of protein.

Based on the presence of proteins of appropriate size, SDS-PAGE analysis of the fractions from the DE-52 column (FIG. 2) confirmed that B was well separated from the two L components, which coeluted. This gel was used to determine which fractions to pool for the next chromatographic step. Fractions 24 to 29 (containing the B component) were pooled and applied to the HA column. Fractions containing B were identified as those which produced complementary hemolysis with L-containing fractions from the DE-52 column. B eluted under the large peak at approximately 160 mM phosphate as illustrated in FIG. 3A.

For isolation of the L components, fractions 9 to 15 were pooled and applied to the HA column. $L_1$ and $L_2$ eluted under the large peaks at around 90 and 125 mM phosphate respectively as illustrated in FIG. 3B. The identities of the L components were established by SDS-PAGE analysis. At this step all three components exhibited single bands on Coomassie Blue stained gels (not shown). The final chromatographic step on the MQ anion exchange column resulted in highly purified preparations of all three components as determined with an SDS-PAGE gel stained with silver as illustrated in FIG. 4. Assuming that the absorbency at 280 nm represented the concentration of the purified component by the HA step, the yields of the components from 4 liters of culture supernatant were 2.2, 2.0, and 2.9 mg of B, $L_1$, and $L_2$ respectively. At the MQ step the yields were 1.4, 0.9, and 1.8 mg respectively. Using subsequently determined extinction coefficients, the yields were as follows for B: HA 1.7mg; MQ 1.0 mg. The yields for $L_1$ were as follows: HA 1.0 mg; MQ 0.5 mg. The yields for $L_2$ were as follows: HA 3.5 mg; MQ 2.2.

Experiment 2

Analysis of Amino-Terminal Amino Acids

Purified proteins were prepared for N-terminal sequence analysis as described by Matsudaira (1990). Electroblotted proteins were cut from the transfer membranes and sent to the Protein/Nucleic Acid Shared Facility at the Cancer Center of the Medical College of Wisconsin for N-terminal sequence analysis by Edman degradation.

Physical characteristics of hemolysin BL components:

Table 1 lists experimentally determined physical characteristics of the components of hemolysin BL. A single band was visible for all three components by SDS-PAGE (FIG. 4) and for the B component by IEF. $L_1$ and $L_2$ each exhibited a second minor band by IEF of pI 5.20 and 5.26 respectively. We do not yet know whether these minor bands represent isoforms of the components or contaminants.

TABLE 1

Physical Characteristics of the Components of Hemolysin BL

| Component | Mol wt[a] | pI[b] | N terminus[c] | E[d] | Seq ID# |
|---|---|---|---|---|---|
| B | 37,800 | 5.34 ± 0.012 | S-E-I-E-Q-T-N-N-G-D-T-A-L | 1.32 | 1 |
| $L_1$ | 38,500 | 5.33 ± 0.008 | x-E-T-I-A-Q-E-Q-K-V-G-N-Y-A-L-G-P-E | 1.85 | 2 |
| $L_2$ | 43,200 | 5.33 ± 0.016 | E-T-Q-x-E-N-M-D-I-x-S | 0.83 | 3 |

[a]Calculated from the SDS-polyacrylamide gel in FIG. 4
[b]Average value for three different IEF gels
[c]x, undetermined residue
[d]Extinction coefficient at 280 nm, 1 cm path length Experiment 3

Vascular Permeability Assay

Vascular permeability activity was assayed as described by Glatz et al. (1974). Rabbits of either 2–3 kg or 4–5 kg were used. The larger animals produced more distinct reactions. Data obtained from different rabbits are reported separately. All activities are reported as averages of duplicate samples.

The components of hemolysin BL were tested individually and in combination for vascular permeability activity in rabbit skin. In a cutaneous edematous reaction, microvascular permeability is compromised, allowing leakage of serum proteins into the interstices with subsequent accumulation of fluid. The reaction can be quantitated by the intravenous injection of Evans blue dye, which binds serum proteins and produces an area of bluing surrounding the injection site of a permeability factor (Tu and Miller, 1992). At high concentrations, the *B. cereus* vascular permeability factor/enterotoxin produces a central area of necrosis within the larger areas of bluing and swelling (Glatz et al., 1974).

Results:

Reference is made to Table 2 which shows the VP activity of hemolysin BL components individually and in combination:

TABLE 2

VP Activity of Hemolysin BL Components Individually and in Combination

| Component(s) injected | Amt injected (μg) Each | Amt injected (μg) Total | Reaction diam (mm)[a] Edema[b] | Reaction diam (mm)[a] Bluing | Reaction diam (mm)[a] Necrosis |
|---|---|---|---|---|---|
| B only | 7.68 | 7.68 | —[c] | — | — |
| $L_1$ only | 7.68 | 7.68 | — | — | — |
| $L_2$ only | 7.86 | 7.68 | — | — | — |
| All | 2.56 | 7.68 | NE[d] | 19.0 | 12.0 |
| All | 1.28 | 3.84 | NE | 18.0 | 10.0 |
| All | 0.64 | 1.92 | 21.5 | 19.0 | 8.5 |
| All | 0.32 | 0.96 | 21.5 | 19.5 | 6.5 |
| All | 0.16 | 0.48 | 20.5 | 12.5 | 4.0 |
| All | 0.08 | 0.24 | 18.0 | 8.0 | — |
| All | 0.04 | 0.12 | 13.0 | 4.5 | — |
| All | 0.02 | 0.06 | — | — | — |
| All | 0.01 | 0.03 | — | — | — |

[a]Average of duplicate samples in the same rabbit
[b]Defined as the raised area surrounding an injection site
[c]—, no reaction visible
[d]NE, edema not seen for these samples. Lesions were flat areas of necrosis surrounded by a ring of bluing.

No dermal reaction was noted after injection of 2.5 ug of each individual component or in the combinations of B+$L_2$ and $L_1$+$L_2$ containing 2.5 ug of each component. The combination of B+$L_1$ produced 14 mm of edema, 3 to 4 mm of bluing, and no necrosis. The combination of all three components produced 13 mm of bluing and 11 mm of necrosis, but no edema. Necrotic activity was not previously seen for hemolysin BL. The edematous reaction of the B+$L_1$ combination was seen previously (Beecher and Macmillan, 1991). The enhancement of the necrotic and bluing responses by addition of $L_2$ is also consistent with previous observations, but the lack of edema was surprising. The dose-response data presented in Table 2 suggest that diminished edema is characteristic of high concentrations of the toxin. Extensive tissue destruction may prevent the retention of fluid, thereby reducing swelling.

In the experiment shown in Table 2, no response occurred with the injection of 7.68 ug of each component individually. This quantity was equal to the highest total protein content in the dose response series. Our observations also indicate that there is cooperative activity between B and $L_1$ and between B+$L_1$ and $L_2$.

The VP data presented here establish clearly that hemolysin BL is the necrotic vascular permeability factor of *B. cereus* and that it is composed of three cooperatively acting proteins that have no activity individually.

Experiment 4

Hemolysis Assays

This experiment was performed to estimate the best working concentration range for the components for specific studies. Gel diffusion assays for hemolysin BL were as described previously (Beecher and Macmillan, 1990; Beecher and Macmillan, 1991). Sheep blood (2.5 to 3% v/v) agar was poured onto GelBondR film (FMC Bioproducts, Rockland, Me.) to 0.15 ml/cm2 so that wells of 3 mm diameter would accommodate samples of 10 ul.

Activity is reported as the distance from the well edge to the outer edge of the hemolysis zone, which was calculated by measuring the zone diameter and subtracting the radius of the well (1.5 mm) from the total zone radius. For estimation of L activity, fractions were placed in wells adjacent to, and equidistant from, wells containing B.

After a period of diffusion (several hours to overnight) the lytic zones between the wells were measured. Activity is expressed as the length in millimeters of these lytic zones. This activity was arbitrarily chosen to give a rough estimate of the level of L activity in fractions. The actual level of each L component cannot presently be determined. Hemolysin BL activity was also determined with a microtiter plate assay similar to that described by Young et al. (1986) . In most experiments, the concentration of one or more of the reaction components was held constant in a series of wells while the other components were varied. Dilutions were prepared either in separate tubes or directly in the microtiter wells. The varying components were added in 50 ul aliquots to their respective wells at concentrations four times the desired final concentrations. The constant components were added in 50 ul aliquots to all wells, also at a concentration four times the final desired concentration.

When all components were varied, they were added to their respective wells in 100 ul aliquots. Hemolysis was initiated by the addition of 100 ul of sheep blood diluted in 50 mM Tris-HCl, 150 mM NaCl, pH 7.4 (TBS) to twice the desired final concentration. The final concentration was one that had an optical density of 0.8 to 0.9 at 630 nm (ca. 2.5% v/v). The assay plate was held at 37° C. and the A630 determined at 15 min intervals. Activity was reported at a time point at which hemolysis was >50% and <90% (generally 1.5 h). For 0% hemolysis controls, samples were 100 ul TBS and for 10.0% hemolysis controls, samples were 100 ul of water containing saponin (Bernheimer, 1988). Values for control samples were taken as averages for six replicates. All samples were in triplicate and the reported values are averages. The microplate reader was blanked against a 100% hemolysis control and percent hemolysis was calculated by the following formula: [($A_{630}$ negative control—$A_{630}$ sample)/$A_{630}$ sample/$A_{630}$ negative control] X 100.

Dose responses of hemolysin BL components in turbidimetric hemolysis assays:

Reference is made to FIG. 5A which depicts a complex dose response curve characteristic of hemolysin BL. All three components were each present at the concentrations indicated on the x-axis. There were two unusual features to this curve. First, the activity plateaued above 350 ng/ml. In a separate experiment (not shown) this plateau was nearly flat up to 2500 ng/ml (the maximum concentration tested). Second, there was a concentration range, between 350 ng/ml and 100 ng/ml, in which activity was greater than at higher concentrations.

The dose response curve for the combination of all three hemolysin BL components (FIG. 5A) is unusual in two respects. First, the activity of hemolytic agents does not generally plateau with increasing concentration, particularly at such a low concentration (Ponder, 1948). Second, the occurrence of a concentration range (between 100 and 300 ng/ml) in which hemolysis is greater than at higher concentrations, combined with the plateau, appears to be a unique phenomenon. Similar, but not identical phenomena have been observed for hemolysis by sodium taurocholate and by sodium glycocholate at pH extremes, and for a combination of colloidal silicic acid and complement (Ponder, 1948).

In the experiments depicted in FIGS. 5B–D, the concentrations of one or more components were held constant and the other components were varied. When the constant component(s) was/were in excess there were significant dose responses only below 40 ng/ml (each component) for $L_1+L_2$, 300 ng/ml for B, 30 ng/ml for $L_1$, and 125 ng/ml for $L_2$. With $B+L_1$ each at 1000 ng/ml there was 15.5% hemolysis in the absence of $L_2$ and $B+L_2$ alone caused 10% lysis. None of the individual components, nor the combination of $L_1+L_2$, caused lysis up to at least 2500 ng/ml each.

Figure 5:
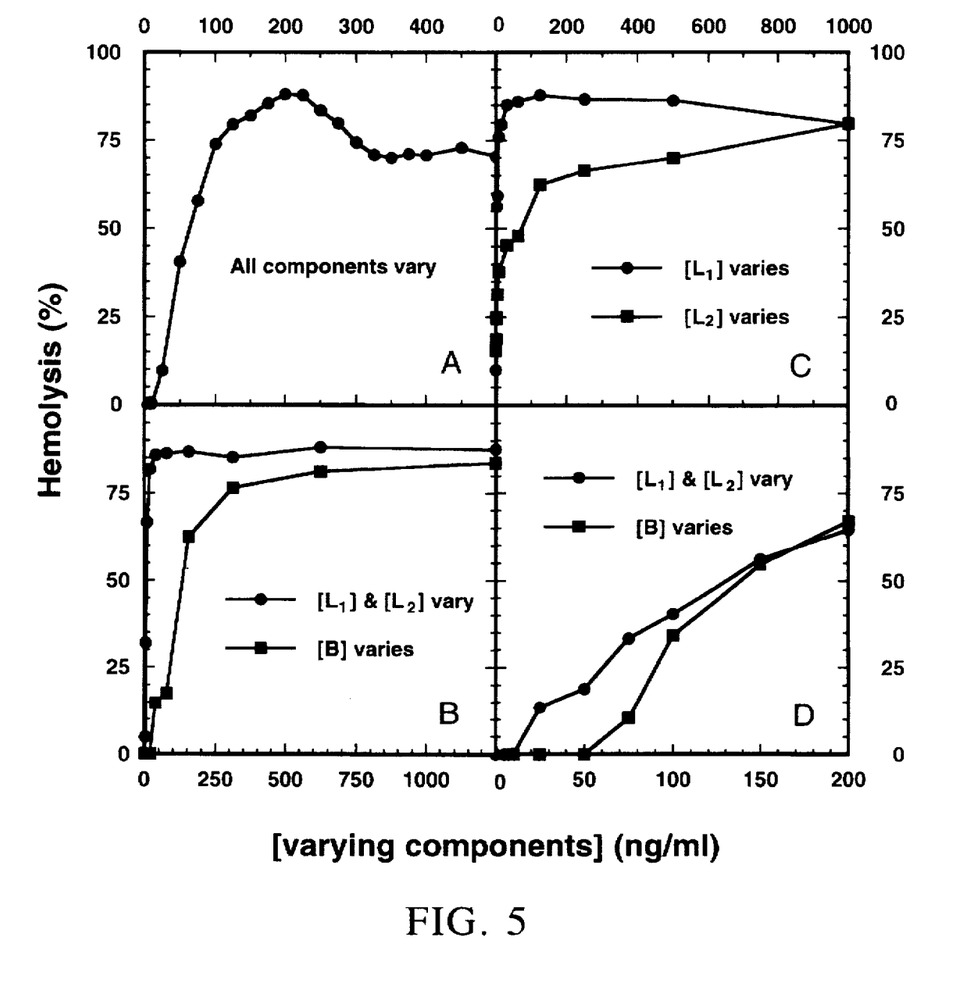

These data suggest that, for working in a dose-dependent concentration range (e.g. when studying the effect of potential inhibitors), each component should be present below about 200 ng/ml. In FIG. 5D, B or $L_1$ and $L_2$ were held at 100 ng/ml and there was a dose response for B and L within the 200 ng/ml range.

Dose-responses of hemolysin BL components in gel diffusion assays:

The dose-response of hemolysin BL in gel diffusion assays was examined. The addition of 10 ng or 1000 ng of each component per well resulted in lytic radii of approximately 1 mm and 3.8 mm respectively. The increase of lytic radius with concentration was asymptotic. Plotting the amount of hemolysin BL per well on a log10 scale produced a roughly linear dose response curve, suggesting that zone size may prove useful for quantitation of hemolysin BL. However, possible effects of variations in the ratios of the components to one another have not been examined.

In another gel diffusion experiment the B component was held at 100 ng/well while the amount of $L_1$ and $L_2$ was varied. Significant activity was detected with 0.5 ng each of $L_1$ and $L_2$ per well. The lytic radius increased sharply to 2.5 ng/well and more gradually to 60 ng/well. Above 60 ng of $L_1$ and $L_2$ per well there was no effect on the size of the lytic zone.

The concentration of blood in a series of gels was varied from 0.5 to 10% and wells in each gel were each loaded with 100 ng of B and 50 ng each of $L_1$ and $L_2$. The distance from the well edge to the edge of the lytic zone varied linearly from 2.2 mm in 10 blood to 3.4 mm in 0.5% blood.

Effect of divalent cations on hemolysis by hemolysin BL:

In turbidimetric assays of hemolysin BL there was a dose-dependent inhibition of hemolysis by Zn++ from 10 to 500 uM. Complete protection was seen for Zn++ concentrations of 500 uM and higher. EDTA (1 mM) prevented the protection of erythrocytes by Zn++. Erythrocytes were not protected by Mg++ or Ca++ up to 25 mM. Complete hemolysis by hemolysin BL at 100 ng/ml typically took greater than 1.5 hours. When erythrocytes were treated for 1.5 h with hemolysin BL (100 ng/ml per component) and Zn++ (500 uM) no lysis occurred, but addition at that time of 1 mM EDTA caused complete lysis in less than one minute.

Experiment 5
Variable Production and Stability of Hemolysin BL Components in *Bacillus cereus*

Little is known about the production kinetics and stabilities of hemolysin BL components (B, $L_1$, $L_2$). *B. cereus* strains from food and non-food sources were grown either for 16 hours at 31° C. on nitrocellulose overlaid on nutrient agar supplemented with 0.15 NaCl and 2% calf serum (colony blots) or aerated for 8.5 hours at 31° C. in BHIG. The colony blots and dot blots of BHIG supernatant were probed with specific polyclonal antibodies to each HBL component. All components were detected at varying levels in 99 of 102 (97%) of the colonies grown 16 hours, but in only 80 (78%) of the 8.5 hour supernatants. At 8.5 hours, only two of the components were detected from three strains and none from 19 strains.

In broth cultures of three isolates, production kinetics and levels varied with strain, temperature, aeration and growth medium. Production was higher at 31° C. with aeration than 25° C. or 37° C. with or without aeration. Strains FM-1 and S1C produced higher levels of all components in BHIG than in CGY; *B. cereus* F837/76 produced higher levels in CGY. The stability of each components also varied. In BHIG, B and $L_2$ increased or remained stable up to 24 hours for all strains; $L_1$ was degraded extensively for S1C and FM-1 but remained stable for F837/76. In CGY, for strains S1C and FM-1, all components were degraded rapidly beginning after 6 hours. No components were detected for FM-1 at 24 hours. For *B. cereus* F837/76, B and $L_1$ remained stable but $L_2$ was slightly degraded after 8 hours. Thus, the production kinetics and stability of hemolysin BL components are highly variable.

Experiment 6

Enterotoxin Activity of Hemolysin BL From *Bacillus cereus*

As stated previously, hemolysin BL is a unique toxin consisting of three different proteins designated B, $L_1$, and $L_2$. All three components are required for maximal activity in all of the biological assays tested so far. It was previously categorized as a diarrheal toxin based on its ability to cause vascular permeability in rabbit skin. Here, HBL was tested for the ability to cause fluid accumulation in the ligated rabbit ileal loop assay, the definitive assay for *B. cereus* diarrheal activity. Samples were injected into ileal loops in 4 New Zealand white rabbits (approximately 1 kg) per experiment. After 5 to 6 hours, fluid accumulation was measured and activity recorded as V/L (the mean of fluid volume to loop-length ratios). Differences in means were analyzed via one-tailed t test. Compared with negative controls (V/L=0.33), injection of all three components caused significant fluid accumulation at 5 ug per component (V/L=0.59, P<0.005) and 25 ug per component (V/L=0.99, P<0.0005). V/L was not significantly different for individual components or binary combinations versus negative controls (P>0.05) and were below the 5 ug dose of all three components (P<0.05). Combined antisera to B and $L_2$ completely inhibited ileal loop activity of *B. cereus* F837/76 culture supernatant. Preimmune serum had no effect on the activity of the supernatant. Hemolysin BL has all of the biological characteristics ascribed to the *B. cereus* enterotoxin, and is 20 to 100 times more potent than previously reported enterotoxin preparations.

It is understood that the present invention is not limited to the particular reagents, steps or methods disclosed herein. Instead it embraces all such modified forms thereof as come within the scope of the claims following the Bibliography.

BIBLIOGRAPHY

Beecher, D. J. and J. D. Macmillan. 1990. *Infect. Immun.*, 58:2220–2227.

Beecher, D. J. and J. D. Macmillan. 1991. *Infect. Immun.*, 59:1778–1784.

Beecher and Wong. 1994. *Infect. Immun.*, 62:980–986.

Bernheimer, A. W. 1988. *Methods Enzymol.*, 165:213–217.

Bitsaev, A. R. and Y. V. Ezepchuk. 1987. *Mol. Genet. Mikrobiol. Virusol.*, 7:18–23.

Blum, H., H. Beier, and H. J. Gross. 1987. *Electrophoresis*, 8:93–99.

Buchanan, R. L., and F. J. Schultz. 1992. *J. Food. Prot.* 55:440–443.

Carlson, C. R., D. A. Caugant, and A.-B. Kolsto. 1994. *Appl. Environ. Microbiol.* 60:1719–1725.

Christiansson, A. 1993. *Neth. Milk Dairy J.* 47:79–87.

Fazekus et al. 1980. *J. Immunol. Methods*, 35:1.

Gilmore, M. S., A. L. Cruz-Rodz, M. Leimeister-Wachter, J. Kreft, and W. Goebel. 1989. *J. Bacteriol.*, 171:744–753.

Glatz, B. A. and J. M. Goepfert. 1977. *J. Food Prot.*, 40:472–474.

Glatz, B. A., W. M. Spira, and J. M. Goepfert. 1974. *Infect. Immun.*, 10:299–303.

Granum, P. E. and H. Nissen. 1993. *FEMS Microbiol. Lett.*, 110:97–100.

Granum, P. E., S. Brynestad, and J. M. Kramer. (Granun et al.). 1993. *Int. J. Food Microbiol.* 17:269–279.

Hames, B. D. 1981. *Gel electrophoresis of proteins: a practical approach.* IRL Press, Washington, D.C.

Harlow, E. and D. Lane. 1988. *Antibodies: a laboratory manual.* Cold Spring Harbor Laboratory, Cold Spring Harbor, N.Y.

Heinrichs, J. H., D. J. Beecher, J. D. Macmillan, and B. A. Zilinskas. 1993. *J. Bacteriol.*, 175:6760–6766.

Kramer, J. M., and R. J. Gilbert. 1989. M. P. Doyle (ed.), *Foodborne bacterial pathogens.* p. 21–70. Marcel Dekker, Inc., N.Y.

Matsudaira, P. 1990. *Meth. Enzymol.* 182:602–612.

Ponder, E. 1948. *Hemolysis and related phenomena.* Grune and Stratton. N.Y.

Stoscheck, C. M. 1990. *Meth. Enzymol.* 182:50–68.

Thompson, N. E., M. J. Ketterhagen, M. S. Bergdoll, and E. J. Shantz. 1984. *Infect. Immun.* 43:887–894.

Tu, A. T. and R. A. Miller. 1992. *J. Toxicol.-Toxin Reviews.* 11:193–239.

Turnbull, P. C. B. 1986. F. Dorner and J. Drews (ed.), *Pharmacology of bacterial toxins.* p. 397–448. Pergamon Press, Oxford.

Turnbull, P. C. B., K. Jorgensen, J. M. Kramer, R. J. Gilbert, and J. M. Parry. 1979a. *J. Clin. Pathol.* 32:289–293.

Turnbull, P. C. B., J. M. Kramer, K. Jorgensen, R. J. Gilbert, and J. Melling. 1979b. *Am. J. Clin. Nut.* 32:219–228.

Young, J. D.-E., L. G. Leong, M. A. DiNome, and Z. A. Cohn. 1986. *Anal. Biochem.* 154:649–654.

---

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS: unknown
        (D) TOPOLOGY: linear     (ii) MOLECULE TYPE: protein     (v) FRAGMENT TYPE: N-terminal     (vi) ORIGINAL SOURCE:
        (A) ORGANISM: Bacillus cereus     (xi) SEQUENCE DESCRIPTION: SEQ ID NO:1:

```
Ser Glu Ile Glu Gln Thr Asn Asn Gly Asp Thr Ala Leu
1               5                   10
```

(2) INFORMATION FOR SEQ ID NO:2:

(i) SEQUENCE CHARACTERISTICS:
        (A) LENGTH: 18 amino acids
        (B) TYPE: amino acid
        (C) STRANDEDNESS: unknown
        (D) TOPOLOGY: linear     (ii) MOLECULE TYPE: protein     (v) FRAGMENT TYPE: N-terminal     (vi) ORIGINAL SOURCE:
        (A) ORGANISM: Bacillus cereus     (xi) SEQUENCE DESCRIPTION: SEQ ID NO:2:

```
Xaa Glu Thr Ile Ala Gln Glu Gln Lys Val Gly Asn Tyr Ala Leu Gly
1               5                   10                  15
Pro Glu
```

(2) INFORMATION FOR SEQ ID NO:3:

(i) SEQUENCE CHARACTERISTICS:
        (A) LENGTH: 11 amino acids
        (B) TYPE: amino acid (C) STRANDEDNESS: unknown
(D) TOPOLOGY: linear (ii) MOLECULE TYPE: protein (v) FRAGMENT TYPE: N-terminal (vi) ORIGINAL SOURCE:
  (A) ORGANISM: Bacillus cereus (xi) SEQUENCE DESCRIPTION: SEQ ID NO:3:

```
Glu Thr Gln Xaa Glu Asn Met Asp Ile Xaa